(12) United States Patent
Rienecker

(10) Patent No.: US 7,864,063 B2
(45) Date of Patent: Jan. 4, 2011

(54) SENSOR ARRANGEMENT FOR DETECTING MOISTURE ON A WINDOW

(75) Inventor: Maik Rienecker, Wollbach (DE)

(73) Assignee: Preh GmbH (DE)

( * ) Notice: Subject to any disclaimer, the term of this patent is extended or adjusted under 35 U.S.C. 154(b) by 251 days.

(21) Appl. No.: 12/018,120

(22) Filed: Jan. 22, 2008

(65) Prior Publication Data
US 2008/0204260 A1 Aug. 28, 2008

Related U.S. Application Data

(63) Continuation of application No. PCT/EP2006/007043, filed on Jul. 18, 2006.

(30) Foreign Application Priority Data

Jul. 19, 2005 (DE) .................. 10 2005 033 557
Jun. 30, 2006 (DE) .................. 10 2006 030 208

(51) Int. Cl.
*G08B 21/00* (2006.01)

(52) U.S. Cl. .............. 340/604; 73/335.04; 73/29.01; 73/170.17; 324/664; 324/658

(58) Field of Classification Search .............. 340/604; 324/664–670, 685; 73/29.01, 170.17, 335.04
See application file for complete search history.

(56) References Cited

U.S. PATENT DOCUMENTS

| | | | |
|---|---|---|---|
| 4,639,831 A * | 1/1987 | Iyoda | 361/286 |
| 4,845,421 A * | 7/1989 | Howarth et al. | 324/688 |
| 4,942,364 A * | 7/1990 | Nishijima et al. | 324/696 |
| 5,668,478 A * | 9/1997 | Buschur | 324/690 |
| 5,780,718 A * | 7/1998 | Weber | 73/29.01 |
| 5,801,307 A * | 9/1998 | Netzer | 73/170.17 |
| 6,094,981 A * | 8/2000 | Hochstein | 73/170.17 |
| 6,373,263 B1 * | 4/2002 | Netzer | 324/665 |
| 6,614,241 B2 * | 9/2003 | Schmitt et al. | 324/664 |
| 7,567,183 B2 * | 7/2009 | Schwenke | 340/602 |

FOREIGN PATENT DOCUMENTS

| | | |
|---|---|---|
| DE | 42 28 737 A1 | 3/1993 |
| DE | 196 02 345 A1 | 8/1997 |
| DE | 197 23 858 A1 | 12/1998 |
| DE | 101 52 998 C2 | 12/2003 |
| DE | 10 2004 050 345 A1 | 4/2006 |
| EP | 0 710 593 A1 | 5/1996 |
| WO | WO 01/81931 A1 | 11/2001 |
| WO | WO 03/060499 A2 | 7/2003 |

* cited by examiner

*Primary Examiner*—Daniel Wu
*Assistant Examiner*—Ryan W Sherwin
(74) *Attorney, Agent, or Firm*—Cantor Colburn LLP

(57) ABSTRACT

An especially simple and economical moisture sensor with temperature compensation is provided. To this end, in addition to a measuring capacitor, a second capacitor is arranged on a window of a motor vehicle, wherein the second capacitor is not affected by the moisture and/or water droplets. For analysis, a differential measurement of the capacitances of the measuring capacitor and of the second capacitor is carried out, from which is determined a degree of wetting of the window not influenced by the window temperature.

7 Claims, 1 Drawing Sheet

SENSOR ARRANGEMENT FOR DETECTING MOISTURE ON A WINDOW

This nonprovisional application is a continuation of International Application No. PCT/EP2006/007043, which was filed on Jul. 18, 2006, and which claims priority to German Patent Application Nos. DE 102005033557 and DE 102006030208, which were filed in Germany on Jul. 19, 2005 and Jun. 30, 2006, respectively, and which are both herein incorporated by reference.

BACKGROUND OF THE INVENTION

1. Field of the Invention

The present invention relates to a sensor arrangement for detecting moisture and/or [water] drops on a window, in particular a windshield of a motor vehicle, according to the preamble of claim 1.

2. Description of the Background Art

Sensor arrangements are used in automobiles, for example, in order to control automatic windshield wipers and/or fans.

DE 196 02 345 A1 discloses a sensor for detecting the moisture on a window of a motor vehicle in which at least one electrically conductive layer is arranged in a certain pattern on an exterior surface of the window. The sensor evaluates the electrical resistance which is present between two layers with different electrical potentials and which changes as the quantity of water on the window changes.

DE 101 52 998 C2 describes a sensor unit for detecting wetting of a window having two sensors that operate on the capacitive principle. One of the sensors is for detecting condensation on the inside of the window, and the other is for sensing condensation on the outside. The sensors are connected to an analysis unit that is integrated in the sensor unit.

DE 197 23 858 A1 describes a device for heating a window in which a window heater is controlled as a function of wetting of the window. This wetting is detected by a moisture sensor, which takes the form of a capacitive sensor, for example.

From EP 710 593 A1 is known a sensor for capacitive measurement of the density of moisture on a window. Arranged on a side of the window facing away from the liquid, or inside the window, are conductive traces that form a capacitor and have a comb-like or finger-like structure. The conductive traces are connected to a measurement device for determining the capacitance.

In none of the known sensors from the prior art cited above is temperature compensation mentioned.

The applicant is aware of temperature compensation for a capacitive rain sensor in which a temperature of the window is measured by means of a separate temperature sensor—for example a resistance thermometer—and is added as a correction value to the capacitance present at the rain sensor. This temperature compensation requires a separate sensor and a relatively great computational effort.

SUMMARY OF THE INVENTION

It is therefore an object of the present invention to provide a sensor arrangement for detecting moisture and/or water drops, in which temperature compensation can be carried out with simple and economical means.

This object is attained according to the invention in that a second capacitor is arranged on the window in order to compensate for temperature differences. As a result of the fact that a second capacitor, which is not influenced by the moisture and/or the water droplets, is arranged on the window to compensate for temperature differences, the capacitance of the second capacitor is only influenced by the temperature, and can enter into the evaluation as a reference value. To this end, a simple differential measurement of the capacitances of the measuring capacitor and of the second capacitor is carried out, from which is determined a degree of wetting of the window not influenced by the window temperature. Only very little computational effort is required for very high precision for this purpose. Moreover, the reference value can be used for evaluating additional measurement results from other measuring capacitors.

The second capacitor has a far simpler structure than an alternative temperature measurement and integrates well into an electrode with the measuring capacitor, so that the compensation can be achieved economically.

The path of the second capacitor's field lines between the electrodes and the surface of the window facing away from the electrodes has the effect that the field lines pass primarily within the window, and therefore are influenced only by the temperature of the window. Consequently, a defined temperature value is available to the control loop that follows the sensors.

The arrangement of the second capacitor on the printed circuit board simplifies fabrication and installation, and also produces a compact sensor arrangement.

The unfolded parallel-plate capacitor is easy to fabricate by applying suitable electrodes on the printed circuit board.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
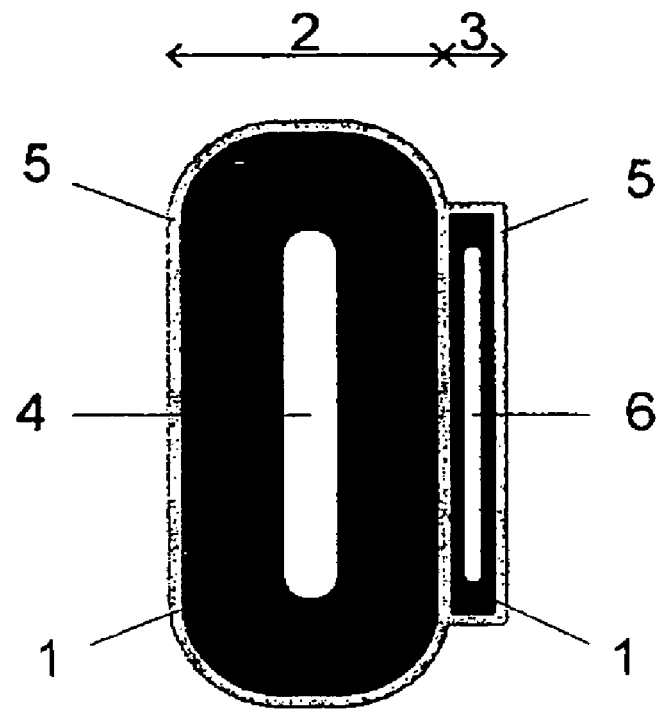
FIG. 1 is a top view of an inventive sensor arrangement.

As is evident from FIG. 1, a measuring capacitor 2 and, adjacent thereto, a second capacitor 3, are arranged next to one another on a first primary surface of a printed circuit board 1 in an arrangement that can be described as parallel.

The measuring capacitor 2 is constructed in the manner of an unfolded capacitor and includes a first electrode 4 in the form of a narrow rectangle with rounded corners. A second electrode 5 is routed around the first electrode 4 in such a manner that an essentially constant spacing is present between the two.

The second capacitor 3 includes a third electrode 6 and the second electrode 5 and has essentially the same construction as the measuring capacitor 2, with the difference that the third electrode 6 is narrower than the first electrode 4, and its spacing from the second electrode 5 is smaller. The second electrode 5 here is designed as a common electrode for the measuring capacitor 2 and the second capacitor 3, and has the shape of a stylized, flattened figure eight.

Figure 2:
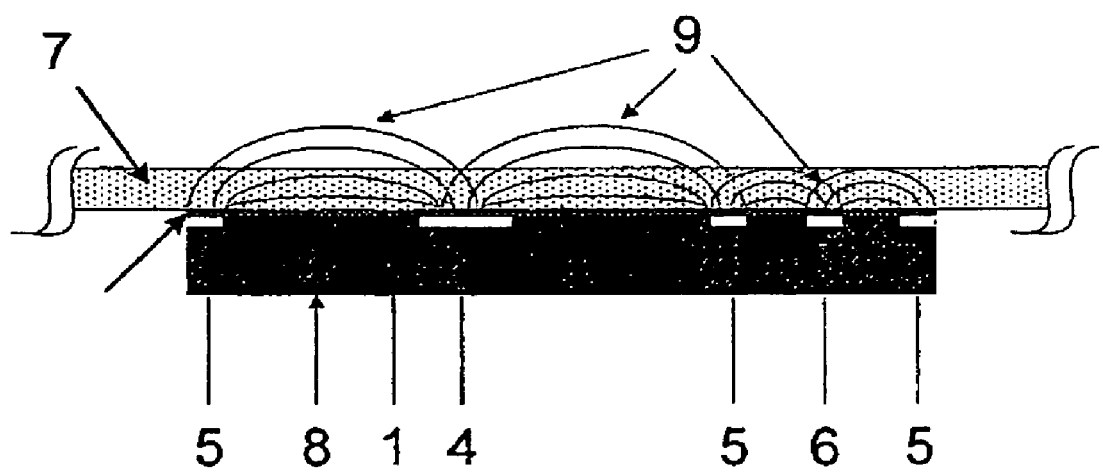
FIG. 2 is a cross-section through the sensor arrangement (enlarged as compared to FIG. 1).

As is evident from FIG. 2, the printed circuit board 1 is attached to a window 7, in particular a windshield of a vehicle, in such a manner that the electrodes 4, 5, 6 rest against the window 7. The electrodes can be connected to a voltage source and are connected to an analysis unit. The electrical terminals and the analysis unit are arranged on a second primary surface of the printed circuit board 1 that faces away from the window 7 and is not shown, wherein the electronic components can be arranged in an area 8 directly on the printed circuit board 1. The analysis unit includes a device for determining the capacitance and means for difference determination.

In operation, for example when the ignition of the vehicle is switched on, voltage is applied to the sensor arrangement. As a result of the voltage, field lines 9, which are shown schematically in FIG. 2, are produced between the electrodes 4, 5, 6. It is important here that the measuring capacitor 2 is laid out such that the associated field lines 9 act at least partially through the window 7 and in the space behind the second primary surface of the window 7. In contrast, the field lines 9 of the second capacitor 3 act exclusively within the window 7 on account of the layout of the second capacitor; thus, the potential of the second capacitor 3 is affected exclusively by the temperature, while external influences, such as raindrops, for example, have no effect thereon. The potentials of the measuring capacitor 2 and the second capacitor 3 are sensed in the analysis unit, and a difference of the potentials is determined. This difference is a measure for moisture and/or drops on the window 7, and is used in a known manner to, for example, switch a windshield wiper on and off.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A sensor arrangement for detecting moisture and/or drops of liquid on a surface of a window, the sensor arrangement comprising: a printed circuit board; a measuring capacitor provided on the printed circuit board for detecting moisture and/or drops; an analysis unit; and a second capacitor whose field lines extend into the window and is arranged on the window in order to compensate for temperature differences, said measuring capacitor comprising a first electrode and a second electrode, said second electrode being implemented as a common electrode for the measuring capacitor and for said second capacitor, said second capacitor comprising a third electrode beside said second electrode and said second capacitor being substantially configured like said measuring capacitor, wherein said second electrode has the shape of a generally stylized flattened figure eight, said second electrode is routed in such a manner about said first electrode that said first electrode and said second electrode are spaced a substantially constant distance apart and said first electrode is configured in the shape of a narrow rectangle with rounded angles.

2. The sensor arrangement according to claim 1, wherein the second capacitor is designed such that its field lines extend between its electrodes and the surface of the window facing away from the electrodes.

3. The sensor arrangement according to claim 1, wherein the second capacitor is arranged on the printed circuit board.

4. The sensor arrangement according to claim 1, wherein the measuring capacitor and the second capacitor are an unfolded capacitor.

5. The sensor arrangement according to claim 1, wherein the analysis unit is arranged on the printed circuit board.

6. The sensor arrangement according to claim 1, wherein the window is a windshield of a motor vehicle.

7. A sensor arrangement for detecting moisture and/or drops of liquid on a surface of a window, the sensor arrangement comprising: a printed circuit board; a measuring capacitor provided on the printed circuit board for detecting moisture and/or drops; an analysis unit; and a second capacitor whose field lines extend into the window and is arranged on the window in order to compensate for temperature differences, said measuring capacitor comprising a first electrode and a second electrode, said second electrode being implemented as a common electrode for the measuring capacitor and for said second capacitor, said second capacitor comprising a third electrode beside said second electrode and said second capacitor being substantially configured like said measuring capacitor, wherein said second electrode comprises two loops, one of the two loops surrounds said first electrode and another one of said two loops surrounds said third electrode.

* * * * *